(12) United States Patent
Gupta et al.

(10) Patent No.: US 7,868,029 B2
(45) Date of Patent: Jan. 11, 2011

(54) PROCESS FOR THE PREPARATION OF 2-AMINO-4,5,6,7-TETRAHYDRO-6-AMINOBENZOTHIAZOLES FROM CYCLOHEXANES AND CYCLOHEXANONES AS INTERMEDIATES

(75) Inventors: Ashwini Kumar Gupta, Mumbai (IN); Balu Aghav, New Panvel (IN); Anil Kumar Tripathi, New Panvel (IN); Abhay Gaitonde, Thane (IN)

(73) Assignee: Generics [UK] Limited, Hertfordshire (GB)

( * ) Notice: Subject to any disclaimer, the term of this patent is extended or adjusted under 35 U.S.C. 154(b) by 235 days.

(21) Appl. No.: 10/527,844

(22) PCT Filed: Sep. 17, 2003

(86) PCT No.: PCT/GB03/04022

§ 371 (c)(1),
(2), (4) Date: Jan. 9, 2006

(87) PCT Pub. No.: WO2004/026850

PCT Pub. Date: Apr. 1, 2004

(65) Prior Publication Data

US 2006/0106224 A1    May 18, 2006

(30) Foreign Application Priority Data

Sep. 17, 2002 (GB) ................. 0221513.5

(51) Int. Cl.
*A61K 31/425* (2006.01)
(52) U.S. Cl. .................................. 514/367
(58) Field of Classification Search .................. 514/367
See application file for complete search history.

(56) References Cited

U.S. PATENT DOCUMENTS

| | | | |
|---|---|---|---|
| 4,731,374 A | 3/1988 | Kobinger et al. | |
| 4,843,086 A | 6/1989 | Griss et al. | |
| 4,886,812 A | 12/1989 | Griss et al. | |
| 5,708,187 A | 1/1998 | Flaugh et al. | |

FOREIGN PATENT DOCUMENTS

| | | | |
|---|---|---|---|
| DE | 3620813 A1 | | 12/1987 |
| EP | 0207696 A1 | | 1/1987 |
| EP | 0207696 A1 | * | 7/1987 |
| EP | 0749962 A1 | | 12/1996 |
| EP | 1008592 A2 | | 6/2000 |
| GB | 2394951 A | * | 5/2004 |
| IL | 77415 A | | 3/1990 |
| WO | 9618395 A1 | | 6/1996 |
| WO | 9959563 A2 | | 11/1999 |
| WO | 02/22590 A1 | | 3/2002 |
| WO | 02/22591 A1 | | 3/2002 |
| WO | WO 02/22590 A1 | * | 3/2002 |
| WO | 2004/026850 A1 | | 4/2004 |

OTHER PUBLICATIONS

Solomons and Fryle Organic Chemistry 9th Edition, 2008, John Wiley and Sons.*
F. Z. Dorwald "Side Reactions in Organic Synthesis: A Guide to Successful Synthesis Design" 2005, Wiley-VCH Verlag GmbH & Co. KGaA, Weinheim.*
Yokum et al Tetrahedron Letters 1997, 38, 4013-4016.*
Jerry March Advanced Organic Chemistry 4th Ed, 1992, pp. 587-590.*
Jerry March Advanced Organic Chemistry 4th Ed, 1992, pp. 1080-1083.*
Avenell et al Bioorg Med Chem Lett 1999, 2715-2720.*
DeKimpe et al The Chemistry of alpha-haloketones, alpha-haloaldehydes and alpha-haloimines 1988, John Wiley & Sons, pp. 1-38.*
International Search Report for International Patent Application No. PCT/GB03/04022, mailed Feb. 18, 2004.
Schneider et al., "Dopamine Autoreceptor Agonists: Resolution and Pharmacological Activity of 2,6-Diaminotetrahydrobenzothiazole and an Aminothiazole Analogue of Apomorphine," *Journal of Medicinal Chemistry*, 1987, 30(3), 494-498.

* cited by examiner

*Primary Examiner*—Janet L Andres
*Assistant Examiner*—John Mabry
(74) *Attorney, Agent, or Firm*—Wolf, Greenfield & Sacks, P.C.

(57) ABSTRACT

The present invention relates to processes for the preparation of 2-amino-4,5,6,7-tetrahydro-6-aminobenzothiazoles (5a) from cyclohexanes (2a) and cyclohexanones (3a) as intermediate.

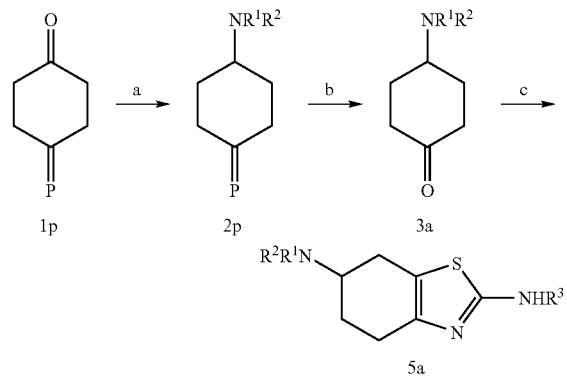

a: reductive amination with $R^1R^2NH$
b: deprotection
c: (i) iodine, $H_2N(C{=}S)NHR^3$; (ii) $OH^-$

10 Claims, 4 Drawing Sheets a: reductive amination with $R^1R^2NH$
b: deprotection
c: (i) iodine, $H_2N(C=S)NHR^3$; (ii) $OH^-$ a: reductive amination with $R^1R^2NH$
b: deprotection
c: (i) iodine, $H_2N(C=S)NHR^3$; (ii) $OH^-$ a: *n*-propylamine, NaCNBH₃, MeOH/HCl
b: aq. HCl/THF
c: (i) iodine, H₂N(C=S)NH₂, ethanol, reflux; (ii) aq. NaOH

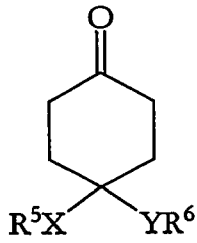

1q

X, Y = O, S or Se
$R^5$, $R^6$ = CO-$R^7$, Si($R^7$)$_3$, or an optionally substituted alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton
$R^7$ = hydrogen or alkyl and/or $XR^5$, $YR^6$ = CN

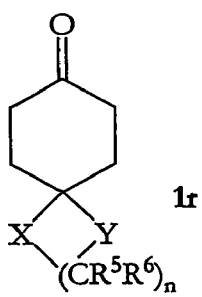

1r

X, Y = O, S, $NR^7$ or Se
n = 2 or 3
$R^5$, $R^6$ = hydrogen, halide, or an optionally substituted alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton
$R^7$ = hydrogen or alkyl

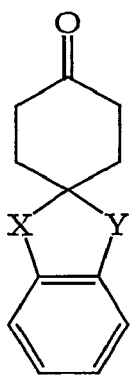

1s

X, Y = O, S or $NR^6$
$R^6$ = hydrogen or alkyl

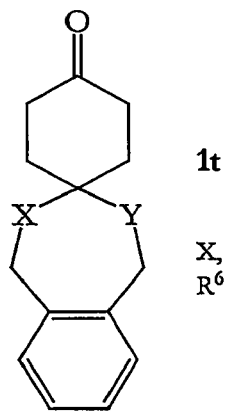

1t

X, Y = O, S or $NR^6$
$R^6$ = hydrogen or alkyl

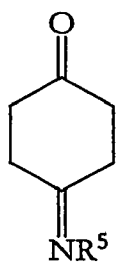

1u $R^5$ = N($R^6$)$_2$ or $OR^6$
$R^6$ = hydrogen, or an optionally substituted alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton

Figure 4

PROCESS FOR THE PREPARATION OF 2-AMINO-4,5,6,7-TETRAHYDRO-6-AMINOBENZOTHIAZOLES FROM CYCLOHEXANES AND CYCLOHEXANONES AS INTERMEDIATES

TECHNICAL FIELD

The present invention relates to processes for the preparation of 2-amino-4,5,6,7-tetrahydro-6-aminobenzothiazoles and to novel cyclohexanes and cyclohexanones for use in these processes.

BACKGROUND ART

Certain 2-amino-4,5,6,7-tetrahydro-6-aminobenzothiazoles are known to have dopamine D-2 activity and are therefore potentially useful as pharmaceuticals for the treatment of psychiatric disorders such as schizophrenia and Alzheimer's disease. One such compound, the dihydrochloride salt of (S)-2-amino-4,5,6,7-tetrahydro-6-(propylamino)-benzothiazole I (pramipexole), is marketed as a pharmaceutical for the treatment of Parkinson's disease. The numbering of pramipexole I is indicated below.

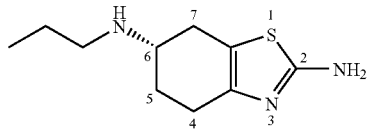

I

Processes for the preparation of 2-amino-4,5,6,7-tetrahydro-6-aminobenzothiazoles are disclosed in U.S. Pat. No. 4,843,086, U.S. Pat. No. 4,886,812 and patent applications WO 02/22590 A1 and WO 02/22591 A1. A procedure to these types of compound is also disclosed by C. S. Schneider and J. Mierau in J. Med. Chem., 1987, vol. 30, pages 494-498.

However, known processes for the preparation of 2-amino-4,5,6,7-tetrahydro-6-aminobenzothiazoles are not satisfactory, particularly for industrial scale manufacture, as they have been found to be low yielding and involve the use of hazardous and difficult to handle reagents such as bromine, hydrazine and potassium chromate.

SUMMARY OF THE INVENTION

A first aspect of the present invention is a process for the preparation of a 2-amino-4,5,6,7-tetrahydro-6-aminobenzothiazole 5a

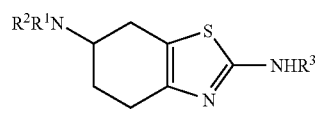

5a or a salt thereof, comprising the steps of:

(a) reductively aminating a protected cyclohexandione 1p with an amine $R^1R^2NH$ to yield a protected 4-amino-cyclohexanone 2p:

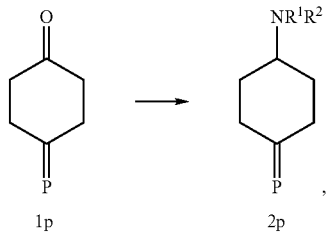

wherein P is a protected ketone functionality, and $R^1$ and $R^2$ are any atom or group or, together with the nitrogen to which they are attached, form a ring;

(b) deprotecting the protected 4-amino-cyclohexanone 2p to yield an unprotected 4-amino-cyclohexanone 3a

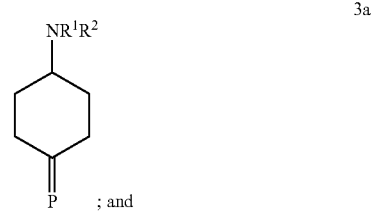

3a (c) treating the unprotected 4-amino-cyclohexanone 3a with iodine and a substituted thiourea $H_2N(C=S)NHR^3$, wherein $R^3$ is any atom or group, to yield the 2-amino-4,5,6,7-tetrahydro-6-aminobenzothiazole 5a or a salt thereof.

For the purposes of the present invention, an "alkyl" group is defined as a monovalent saturated hydrocarbon, which may be straight-chained or branched, or be or include cyclic groups. Examples of alkyl groups are methyl, ethyl, n-propyl, i-propyl, n-butyl, i-butyl, t-butyl and n-pentyl groups. Preferably an alkyl group is straight-chained or branched and does not include any heteroatoms in its carbon skeleton. Preferably an alkyl group is a $C_1$-$C_{12}$ alkyl group, which is defined as an alkyl group containing from 1 to 12 carbon atoms. More preferably an alkyl group is a $C_1$-$C_6$ alkyl group, which is defined as an alkyl group containing from 1 to 6 carbon atoms. An "alkylene" group is similarly defined as a divalent alkyl group.

An "alkenyl" group is defined as a monovalent hydrocarbon, which comprises at least one carbon-carbon double bond, which may be straight-chained or branched, or be or include cyclic groups. Examples of alkenyl groups are vinyl, allyl, but-1-enyl and but-2-enyl groups. Preferably an alkenyl group is straight-chained or branched and does not include any heteroatoms in its carbon skeleton. Preferably an alkenyl group is a $C_2$-$C_{12}$ alkenyl group, which is defined as an alkenyl group containing from 2 to 12 carbon atoms. More preferably an alkenyl group is a $C_2$-$C_6$ alkenyl group, which is defined as an alkenyl group containing from 2 to 6 carbon atoms. An "alkenylene" group is similarly defined as a divalent alkenyl group.

An "alkynyl" group is defined as a monovalent hydrocarbon, which comprises at least one carbon-carbon triple bond, which may be straight-chained or branched, or be or include cyclic groups. Examples of alkynyl groups are ethynyl, propargyl, but-1-ynyl and but-2-ynyl groups. Preferably an alkynyl group is straight-chained or branched and does not include any heteroatoms in its carbon skeleton. Preferably an alkynyl group is a $C_2$-$C_{12}$ alkynyl group, which is defined as an alkynyl group containing from 2 to 12 carbon atoms. More preferably an alkynyl group is a $C_2$-$C_6$ alkynyl group, which is defined as an alkynyl group containing from 2 to 6 carbon atoms. An "alkynylene" group is similarly defined as a divalent alkynyl group.

An "aryl" group is defined as a monovalent aromatic hydrocarbon. Examples of aryl groups are phenyl, naphthyl, anthracenyl and phenanthrenyl groups. Preferably an aryl group does not include any heteroatoms in its carbon skeleton. Preferably an aryl group is a $C_4$-$C_{14}$ aryl group, which is defined as an aryl group containing from 4 to 14 carbon atoms. More preferably an aryl group is a $C_6$-$C_{10}$ aryl group, which is defined as an aryl group containing from 6 to 10 carbon atoms. An "arylene" group is similarly defined as a divalent aryl group.

Where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

For the purposes of this invention, an optionally substituted alkyl, alkenyl, alkynyl, aryl, arylalkyl, arylalkenyl, arylalkynyl, alkylaryl, alkenylaryl or alkynylaryl group may be substituted with one or more of —F, —Cl, —Br, —I, —$CF_3$, —$CCl_3$, —$CBr_3$, —$CI_3$, —OH, —SH, —$NH_2$, —CN, —$NO_2$, —COOH, —$R^4$—O—$R^5$, —$R^4$—S—$R^5$, —$R^4$—SO—$R^5$, —$R^4$—$SO_2$—$R^5$, —$R^4$—$SO_2$—$OR^5$, —$R^4O$—$SO_2$—$R^5$, —$R^4$—$SO_2$—$N(R^5)_2$, —$R^4$—$NR^5$—$SO_2$—$R^5$, —$R^4O$—$SO_2$—$OR^5$, —$R^4O$—$SO_2$—$N(R^5)_2$, —$R^4$—$NR^5$—$SO_2$—$OR^5$, —$R^4$—$NR^5$—$SO_2$—$N(R^5)_2$, —$R^4$—$N(R^5)_2$, —$R^4$—$N(R^5)_3^+$, —$R^4$—$P(R^5)_2$, —$R^4$—$Si(R^5)_3$, —$R^4$—CO—$R^5$, —$R^4$—CO—$OR^5$, —$R^4O$—CO—$R^5$, —$R^4$—CO—$N(R^5)_2$, —$R^4$—$NR^5$—CO—$R^5$, —$R^4O$—CO—$OR^5$, —$R^4O$—CO—$N(R^5)_2$, —$R^4$—$NR^5$—CO—$OR^5$, —$R^4$—$NR^5$—CO—$N(R^5)_2$, —$R^4$—CS—$R^5$, —$R^4$—CS—$OR^5$, —$R^4O$—CS—$R^5$, —$R^4$—CS—$N(R^5)_2$, —$R^4$—$NR^5$—CS—$R^5$, —$R^4O$—CS—$OR^5$, —$R^4O$—CS—$N(R^5)_2$, —$R^4$—$NR^5$—CS—$OR^5$, —$R^4$—$NR^5$—CS—$N(R^5)_2$ or —$R^5$. In this context, —$R^4$— is independently a chemical bond, a $C_1$-$C_{10}$ alkylene, $C_1$-$C_{10}$ alkenylene or $C_1$-$C_{10}$ alkynylene group. —$R^5$ is independently hydrogen, unsubstituted $C_1$-$C_6$ alkyl or unsubstituted $C_6$-$C_{10}$ aryl. Optional substituent(s) are not taken into account when calculating the total number of carbon atoms in the parent group substituted with the optional substituent(s).

Any optional substituent may be protected. Suitable protecting groups for protecting optional substituents are known in the art, for example from "Protective Groups in Organic Synthesis" by T. W. Greene and P. G. M. Wuts (Wiley-Interscience, $2^{nd}$ edition, 1991).

For the purposes of this invention, a "salt" is any acid addition salt, preferably a pharmaceutically acceptable acid addition salt, including but not limited to a hydrohalogenic acid salt such as hydrofluoric, hydrochloric, hydrobromic and hydroiodic acid salt; an inorganic acid salt such as nitric, perchloric, sulfuric and phosphoric acid salt; an organic acid salt such as a sulfonic acid salt (for example methanesulfonic, trifluoromethanesulfonic, ethanesulfonic, isethionic, benzenesulfonic, p-toluenesulfonic or camphorsulfonic acid salt), acetic, malic, fumaric, succinic, citric, tartaric, benzoic, gluconic, lactic, mandelic, mucic, pamoic, pantothenic, oxalic and maleic acid salt; and an aminoacid salt such as ornithinic, glutamic and aspartic acid salt. The acid addition salt may be a mono- or di-acid addition salt. A preferred salt is a di-hydrohalogenic, di-sulphuric, di-phosphoric or di-organic acid salt. A most preferred salt is a di-hydrochloric acid salt.

P is a protected ketone functionality. Suitable protecting groups are commonly known in the art, for example from Chapter 4 of "Protective Groups in Organic Synthesis" by T. W. Greene and P. G. M. Wuts (Wiley-Interscience, $2^{nd}$ edition, 1991).

Preferably the protected cyclohexandione 1p is an acyclic ketal or derivative 1q, a cyclic ketal or derivative 1r, 1s or 1t, or a hydrazone or oxime 1u, as shown in FIG. 4. More preferably 1p is a cyclic ketal 1r, most preferably 1p is a monoethyleneketal 1, as shown in FIGS. 2 and 3.

$R^1$, $R^2$ and $R^3$ can be any atom or group. Preferably $R^1$ and $R^2$ are not amine protecting groups. Amine protecting groups are commonly known in the art, for example from Chapter 7 of "Protective Groups in Organic Synthesis" by T. W. Greene and P. G. M. Wuts (Wiley-Interscience, $2^{nd}$ edition, 1991). Most preferably one of $R^1$ and $R^2$ is hydrogen and the other of $R^1$ and $R^2$ is an optionally substituted alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton. Such an optionally substituted alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton, does not encompass carbonyl —CO—R groups, wherein R is any atom or group.

Optionally $R^1$, $R^2$ and $R^3$ are independently hydrogen or an optionally substituted alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton.

Optionally $R^1$, $R^2$ and $R^3$ are independently an alkyl, alkenyl, alkynyl, aryl, arylalkyl, arylalkenyl, arylalkynyl, alkylaryl, alkenylaryl or alkynylaryl group, which may include one or more heteroatoms N, O or S in its carbon skeleton, and which may be optionally substituted with one or more of —F, —Cl, —Br, —I, —$CF_3$, —$CCl_3$, —$CBr_3$, —$CI_3$, —OH, —SH, —$NH_2$, —CN, —$NO_2$, —COOH, —$R^4$—O—$R^5$, —$R^4$—S—$R^5$, —$R^4$—SO—$R^5$, —$R^4$—$SO_2$—$R^5$, —$R^4$—$N(R^5)_2$, —$R^4$—$Si(R^5)_3$, —$R^4$—CO—$R^5$, —$R^4$—CO—$OR^5$, —$R^4O$—CO—$R^5$, —$R^4$—CO—$N(R^5)_2$, —$R^4$—$NR^5$—CO—$R^5$, —$R^4$—CS—$R^5$ or —$R^5$, wherein $R^4$— is independently a chemical bond, a $C_1$-$C_{10}$ alkylene, $C_1$-$C_{10}$ alkenylene or $C_1$-$C_{10}$ alkynylene group, and $R^5$ is independently hydrogen, unsubstituted $C_1$-$C_6$ alkyl or unsubstituted $C_6$-$C_{10}$ aryl.

Optionally $R^1$, $R^2$ and $R^3$ are independently an alkyl, alkenyl, alkynyl, aryl, arylalkyl, arylalkenyl, arylalkynyl, alkylaryl, alkenylaryl or alkynylaryl group, which does not include any heteroatoms in its carbon skeleton, and which may be optionally substituted with one or more of —F, —Cl, —Br, —I, —$CF_3$, —$CCl_3$, —$CBr_3$, —$CI_3$, —OH, —SH, —$NH_2$, —CN, —$NO_2$, —COOH, —$OR^5$, —$SR^5$, —SO—$R^5$, —$SO_2$—$R^5$, —$N(R^5)_2$, —$Si(R^5)_3$, —CO—$R^5$, —CO—$OR^5$, —O—CO—$R^5$, —CO—$N(R^5)_2$, —$NR^5$—CO—$R^5$, —CS—$R^5$ or —$R^5$, wherein $R^5$ is independently hydrogen, unsubstituted $C_1$-$C_6$ alkyl or unsubstituted $C_6$-$C_{10}$ aryl.

Preferably $R^1$, $R^2$ and $R^3$ are independently hydrogen or an unsubstituted alkyl, aryl or heteroaryl group, which does not include any heteroatoms N, O or S in its carbon skeleton. More preferably, $R^1$, $R^2$ and $R^3$ are independently hydrogen or an unsubstituted $C_{1-10}$ alkyl group. More preferably, $R^1$, $R^2$ and $R^3$ are independently hydrogen or an unsubstituted $C_{1-6}$ alkyl group. More preferably, one of $R^1$ and $R^2$ is hydrogen and the other of $R^1$ and $R^2$ is an unsubstituted $C_{1-6}$ alkyl group, and $R^3$ is hydrogen. Most preferably, one of $R^1$ and $R^2$ is hydrogen and the other of $R^1$ and $R^2$ is n-propyl, and $R^3$ is hydrogen.

Alternatively, $R^1$ and $R^2$ can, together with the nitrogen to which they are attached, form a ring. Optionally —$NR^1R^2$ together form an optionally substituted heterocycloalkyl, heterocycloalkenyl or heteroaryl ring. Optionally —$NR^1R^2$ together form

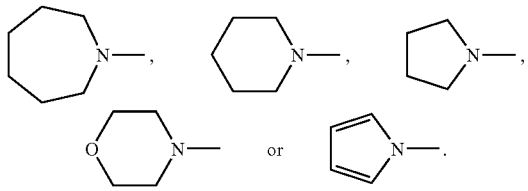

Preferably the reductive amination of step (a) is carried out with NaCNBH$_3$.

A second aspect of the present invention is a 4-amino-cyclohexanone-ethyleneketal 2a or a 4-amino-cyclohexanone 3a

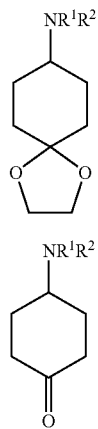

for use in a process of the first aspect of the present invention. $R^1$ and $R^2$ are as defined above with reference to the first aspect of the present invention. Preferably one of $R^1$ and $R^2$ is hydrogen and the other of $R^1$ and $R^2$ is n-propyl.

A third aspect of the present invention is a 2-amino-4,5,6,7-tetrahydro-6-aminobenzothiazole 5a

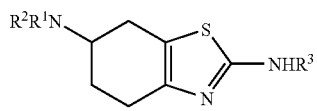

or a salt thereof, obtained by a process of the first aspect of the present invention. $R^1$, $R^2$ and $R^3$ are as defined above with reference to the first aspect of the present invention. Preferably one of $R^1$ and $R^2$ is hydrogen and the other of $R^1$ and $R^2$ is n-propyl, and $R^3$ is hydrogen. Preferably the compound is a di-hydrochloric acid salt.

The 2-amino-4,5,6,7-tetrahydro-6-aminobenzothiazoles 5a or salts thereof have at least one chiral centre and can therefore exist in the form of various stereoisomers. The present invention embraces all of these stereoisomers and mixtures thereof. Mixtures of these stereoisomers can be resolved by conventional methods, for example, chiral chromatography, fractional recrystallisation, derivatisation to form diastereomers and subsequent resolution, and resolution using enzymes.

The 2-amino-4,5,6,7-tetrahydro-6-aminobenzothiazole 5a or salt thereof of the present invention preferably comprises at least 95% of the (R)- or the (S)-enantiomer, preferably at least 98% of the (R)- or the (S)-enantiomer, and mote preferably at least 99% of the (R)- or the (S)-enantiomer. Generally, the (S)-enantiomer is the preferred enantiomer.

The 2-amino-4,5,6,7-tetrahydro-6-aminobenzothiazole 5a or salt thereof may be used as a medicament, preferably for the treatment of a psychiatric or neurological disorder such as schizophrenia, Alzheimer's disease or Parkinson's disease.

A fourth aspect of the present invention is a pharmaceutical composition, comprising 2-amino-4,5,6,7-tetrahydro-6-aminobenzothiazole 5a or salt thereof and a pharmaceutically acceptable carrier or diluent. Preferably the pharmaceutical composition is suitable for the treatment of a psychiatric or neurological disorder such as schizophrenia, Alzheimer's disease or Parkinson's disease.

A fifth aspect of the present invention is a method of treating a psychiatric or neurological disorder such as schizophrenia, Alzheimer's disease or Parkinson's disease, comprising administering a therapeutically effective amount of a 2-amino-4,5,6,7-tetrahydro-6-aminobenzothiazole 5a or a salt thereof to a subject in need of such treatment.

BRIEF DESCRIPTION OF THE DRAWINGS

FIG. 4 illustrates preferred protected ketone functionalities P.

DETAILED DESCRIPTION OF THE INVENTION

Figure 1:
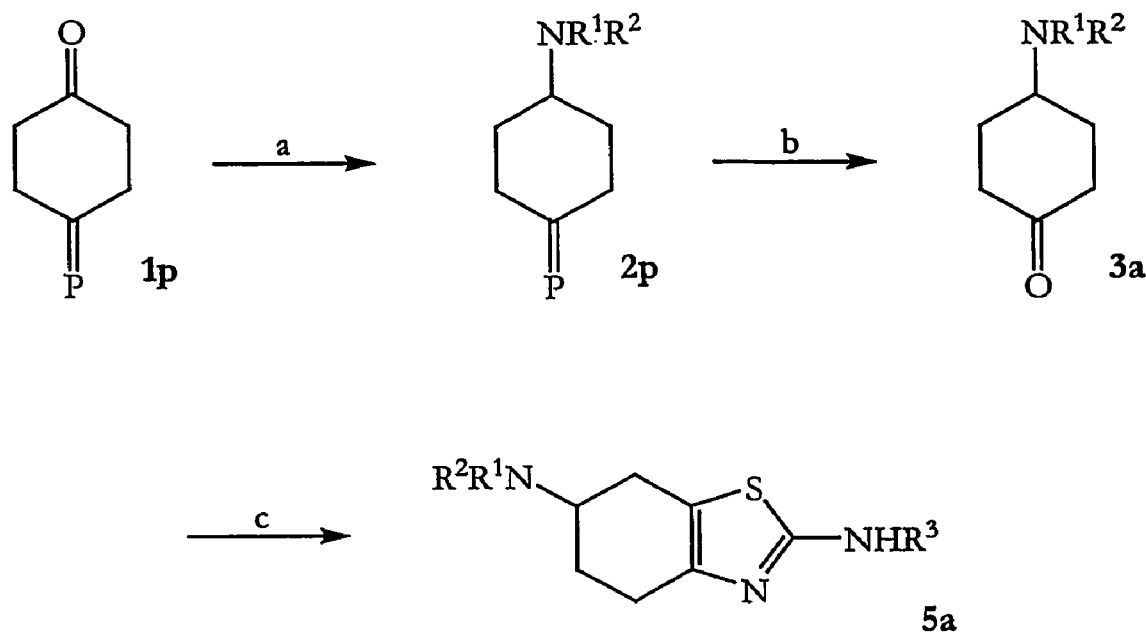
FIG. 1 is a schematic illustration of the process of the present invention.

The inventors have found that processes for the preparation of 2-amino-4,5,6,7-tetrahydro-6-aminobenzothiazoles 5a are greatly improved by the process outlined in FIG. 1, wherein $R^1$ and $R^2$ can be any atom or group or, together with the nitrogen to which they are attached, form a ring, and wherein $R^3$ can be any atom or group. $R^1$, $R^2$ and $R^3$ are preferably hydrogen or an unsubstituted alkyl, aryl or heteroaryl group.

The process outlined in FIG. 1 is short, utilises a readily available starting material, a protected cyclohexandione 1p, and does not require any hazardous chemical reagents. Each step of the process is high yielding and affords products of very high purity.

Therefore a first aspect of the current invention is a process for the preparation of 2-amino-4,5,6,7-tetrahydro-6-aminobenzothiazoles 5a by the process specified in FIG. 1.

It has been disclosed in prior art documents WO 02/22590 and WO 02/22591 that, in practice, compounds of formula 5a, comprising a primary amino or a secondary alkylamino group, cannot be prepared directly from the corresponding ketones 3a. The process shown in FIG. 1, however, illustrates that the process of the current invention does indeed allow a compound 5a to be prepared from ketones 3a directly without the requirement of preparing and isolating an α-haloketone of formula 4, where X is a halide such as chloride or bromide, or the requirement of a protecting group on the nitrogen atom of the amine substituent —NR¹R² of the ketone 3a.

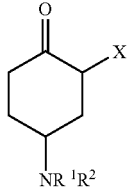

4

Therefore, in a preferred embodiment of the present invention, the α-haloketone of formula 4 is not isolated. Moreover, in a preferred embodiment of the present invention, the nitrogen atom of the amine substituent —NR¹R² of the ketone 3a is not protected.

Figure 2:
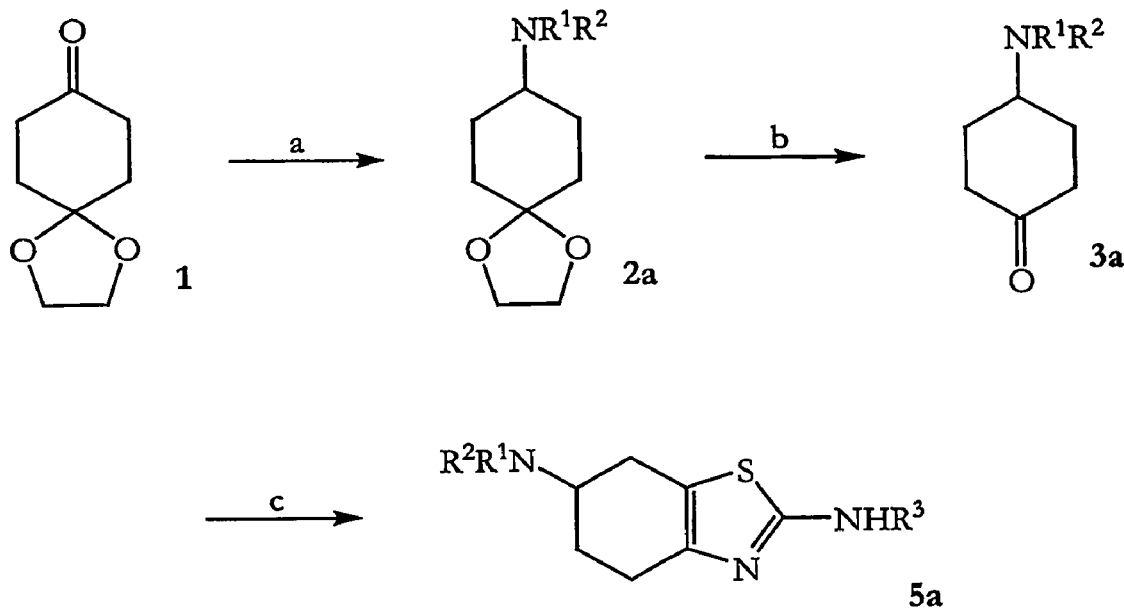
FIGS. 2 and 3 are schematic illustrations of preferred processes of the present invention.
Figure 3:
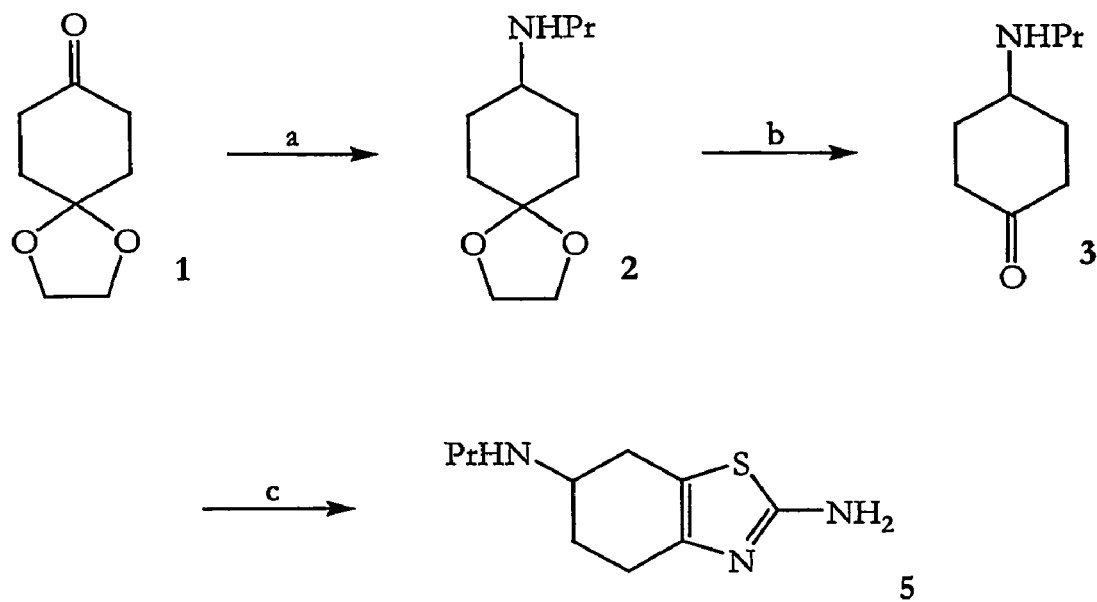

In a preferred embodiment of the first aspect of the invention, cyclohexandione is protected as a cyclohexandione monoethyleneketal 1, as shown in FIGS. 2 and 3.

A further preferred embodiment of the first aspect of the invention is a process for the preparation of 2-amino-4,5,6,7-tetrahydro-6-(propylamino)-benzothiazole 5, as outlined in FIG. 3.

The process outlined in FIG. 3 can readily be adapted to afford pramipexole I or its salts, for example by resolution of compound 5. Methods for resolving enantiomers are well known in the art and include, for example, chiral chromatography, fractional recrystallisation, derivatisation to form diastereomers and subsequent resolution, and resolution using enzymes.

A further aspect of the invention is therefore pramipexole I and its salts, when prepared by a process according to the current invention.

Further aspects of the invention include novel compounds of the formula 2a or 3a, wherein R¹ and R² are as defined above, which are useful intermediates in the synthesis of 2-amino-4,5,6,7-tetrahydro-6-aminobenzothiazoles 5a.

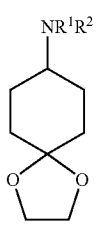

2a

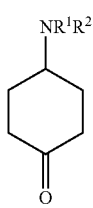

3a

Preferred embodiments of these aspects are compounds 2 and 3, as shown in FIG. 3.

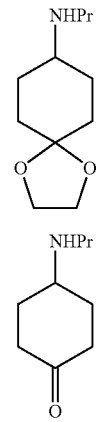

2

3

The process outlined in FIG. 3 is an example of a procedure comprising the process of the current invention and detailed procedures for this process are found in the experimental section. Compounds of the current invention are also exemplified in FIG. 3 and in the experimental section.

The process of the present invention is short, utilises readily available starting materials and does not involve the use of hazardous or difficult to handle reagents such as bromine, hydrazine or potassium chromate. Each step of the process of the present invention is high yielding and affords products of very high purity. Thus the process is easy to scale up for industrial scale manufacturing. Optionally 2-amino-4,5,6,7-tetrahydro-6-aminobenzothiazoles 5a and salts thereof may be manufactured in batches of 5 kg or more, or even 10 kg or more.

EXPERIMENTAL PROCEDURE 4-n-Propylamino-cyclohexanone-ethyleneketal 2

A mixture of n-propyl amine (162 ml, 1.474 mol) in methanol (500 ml) was chilled to 0-5° C. To this solution was added methanolic hydrochloric acid (155 ml, 44.47%) dropwise over a period of 30 minutes to achieve a pH of 6-7. Cyclohexandione monoethyleneketal 1 (100 g, 0.641 mol) was charged at 5° C. and the reaction was stirred for 15 minutes. Sodium cyanoborohydride (60 g, 0.952 mol) was added in 15 minutes at 5° C. The pH increased to about 8 and methanolic hydrochloric acid (15 ml, 44.47%) was added to bring the pH to 6-7. The reaction was allowed to come to 24-26° C. Stirring was continued for 2 hours. Methanol was distilled off (450 ml). Sodium carbonate (95 g, 0.896 mol) was dissolved in water (850 ml) and charged to the reaction mass at ambient temperature in one shot. The reaction mass was extracted with dichloromethane (2500 ml). The dichloromethane layers were combined and dried over sodium sulfate (8.5 g). The dichloromethane layer was concentrated to dryness at 40° C. and 15 mbar pressure. The product 2 was light yellow viscous oil. The weight of the product 2 obtained was 135 g (105.8%); GC purity 97.74%.

$^1$H NMR (δ ppm): 0.9-1.0 (t, 3H, CH$_3$ of nPr); 1.5-1.7 (m, 7H, C$\underline{H}_2$CH$_3$ of nPr and 5H of cyclohexyl ring); 1.75-1.85 (m, 2H, 2H of cyclohexyl ring); 1.95-2.05 (m, 1H, 1H of cyclohexyl ring); 2.75 (t, 2H, C$\underline{H}_2$CH$_2$CH$_3$ of nPr); 3.75-3.85 (m, 1H, NHC$\underline{H}$); 3.9 (s, 2H, CH$_2$ of ethylene ketal) and 4.0 (s, 2H, CH$_2$ of ethylene ketal).

$^{13}$C NMR (δ ppm): 11.7 (CH$_3$ of nPr); 21.8 (CH$_2$CH$_3$ of nPr); 28.5 (C-3 and C-5); 33.1 (C-2 and C-6); 48.3 (CH$_2$CH$_2$CH$_3$ of nPr); 55.8 (C-4); 64.5 (C of ethylene ketal); 64.6 (C of ethylene ketal); 108.1 (C-1).

4-n-Propylamino-cyclohexanone 3

4-N-propylamino-cyclohexanone-ethyleneketal 2 (134 g, 0.673 mol) was taken in tetrahydrofuran (268 ml) and cooled to 4-6° C. Concentrated hydrochloric acid (178 ml, 2.01 mol) was diluted with water (2144 ml) and the mixture was cooled to 4° C. This diluted hydrochloric acid was added to the reaction mixture at 4-6° C. in 15 minutes. The reaction was allowed to come to 24-26° C. and stirring was continued for 24 hours. The reaction mass (2750 ml) was concentrated to 1800 ml at 50° C. and 35 mbar pressure. Sodium carbonate (148 g, 1.4 mol) was added to achieve pH 10. The reaction mixture was extracted with dichloromethane (3670 ml). The dichloromethane layers were combined and dried over sodium sulfate (20 g). The dichloromethane layer was concentrated to dryness at 40° C. and 15 mbar pressure. The product 3 was yellow viscous oil. The weight of the product 3 obtained was 52.5 g (52.84%); GC purity 86.07%.

$^1$H NMR (δ ppm): 0.9-1.0 (t, 3H, CH$_3$ of nPr); (m, 2H, CH$_2$CH$_3$ of nPr); 1.6-1.75 (m, 2H, 2H of cyclohexyl ring); 2.05-2.15 (m, 2H, 2H of cyclohexyl ring); 2.2-2.3 (m, 2H, 2H of cyclohexyl ring); 2.4-2.55 (m, 2H, 2H of cyclohexyl ring); 2.55-2.65 (t, 2H, CH$_2$CH$_2$CH$_3$ of nPr); 2.9-3.0 (m, 1H, NHCH).

$^{13}$C NMR (δ ppm): 12.3 (CH$_3$ of nPr); 24.0 (CH$_2$CH$_3$ of nPr); 32.6 (C-3 and C-5); 39.1 (C-2 and C-6); 50.0 (CH$_2$CH$_2$CH$_3$ of nPr); 54.4 (C-4); 211.9 (C-1).

2-Amino-6-n-propylamino-5,6,7,8-tetrahydrobenzthiazole 5

4-n-Propylamino-cyclohexanone 3 (5 g, 32.26 mmol) was charged in absolute ethanol (50 ml) at 24-26° C. Iodine (8.5 g, 33.5 mmol) was added to it under stirring followed by thiourea (5 g, 65.7 mmol) at 24-26° C. The reaction mass was refluxed for 32 hours. Heating was stopped and the reaction mass was allowed to cool to 24-26° C. It was maintained at that temperature for 20 hours. 2-Amino-6-n-propylamino-5,6,7,8-tetrahydrobenzthiazole dihydroiodide salt crystallized out of the solution. Ethanol (30 ml) was distilled out on the rotavapor at 50° C. and 100 mbar. Acetone (50 ml) was added and the solid was filtered. The solid was dried at 40° C. and 15 mbar. The weight of the product obtained was 8.5 g (56%); HPLC purity 94.97%.

$^1$H NMR (δ ppm): 0.9-1.0 (t, 3H, CH$_3$ of nPr) 1.6-1.8 (m, 2H, CH$_2$CH$_3$ of nPr); 2.0 (m, 1H, H-7a); 2.35 (m, 1H, H-7b); 2.7 (m, 3H, H-5a, H-8a, H-8b); 3.1 (m, 3H, H-5b and CH$_2$CH$_2$CH$_3$ of nPr); 3.7 (m, 1H, NHCH).

$^{13}$C NMR (δ ppm): 12.0 (CH$_3$ of nPr); 21.0 (CH$_2$CH$_3$ of nPr); 22.2 (C-7); 25.5 and 26.8 (C-5 and C-8); 48.7 (CH$_2$CH$_2$CH$_3$ of nPr); 54.7 (C-6); 113.0 (C-4); 134 (C-9); 171.2 (C-2).

Mass Spec: M$^+$ 211 (expected 211).

The 2-amino-6-n-propylamino-5,6,7,8-tetrahydrobenzthiazole dihydroiodide salt formed above (50 g, 107.1 mmol) was dissolved in water (200 ml). The solution was cooled to 4° C. and solid sodium hydroxide (50 g, 1.25 mol) was added in 15 minutes. The reaction was stirred for 1 hour at 24-26° C. and the solid that precipitated out was filtered and dried at 40° C. and 15 mbar. The weight of the product 5 obtained was 17.07 g (75.5%); HPLC purity 99.88%.

$^1$H NMR (δ ppm): 0.9-1.0 (t, 3H, CH$_3$ of nPr); 1.5-1.6 (m, 2H, CH$_2$CH$_3$ of nPr); 2.1 (m, 1H, H-7a); 2.3 (m, 1H, H-7b); 2.5-2.6 (m, 5H, H-5a, H-5b, H-8a, H-8b and CHCH$_2$CH$_3$ of nPr); 2.9 (m, 2H, H-6 and CHCH$_2$CH$_3$ of nPr).

$^{13}$C NMR (δ ppm): 12.0 (CH$_3$ of nPr); 24.6 (CH$_2$CH$_3$ of nPr); 26.6 (C-7); 30.7 and 30.9 (C-5 and C-8); 50.7 (CH$_2$CH$_2$CH$_3$ of nPr); 56.2 (C-6); 116.0 (C-4); 145 (C-9); 170.4 (C-2).

Mass Spec: M$^+$ 211 (expected 211).

It will be understood that the present invention has been described above by way of example only. The examples are not intended to limit the scope of the invention. Various modifications and embodiments can be made without departing from the scope of the invention, which is defined by the following claims.

The invention claimed is:

1. A process for the preparation of a 2-amino-4,5,6,7-tetrahydro-6-aminobenzothiazole 5a:

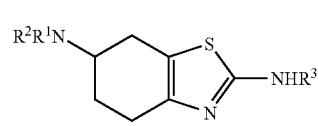

or an enantiomer or a salt thereof, comprising the steps of:
(a) reductively aminating a protected cyclohexandione 1p with an amine R$^1$R$^2$NH to yield a protected 4-aminocyclohexanone 2p:

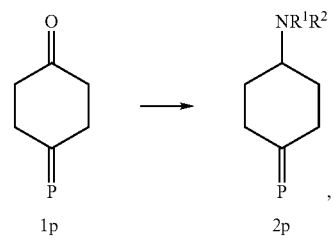

wherein P is a protected ketone functionality, and wherein one of R$^1$ and R$^2$ is hydrogen and the other of R$^1$ and R$^2$ is n-propyl;
(b) deprotecting the protected 4-amino-cyclohexanone 2p to yield an unprotected 4-amino-cyclohexanone 3a:

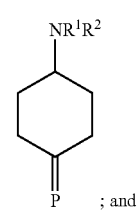

; and (c) treating the unprotected 4-amino-cyclohexanone 3a with iodine and a thiourea H$_2$N(C=S)NHR$^3$, wherein R$^3$ is hydrogen or a C$_1$-C$_{12}$ alkyl to yield the 2-amino-4,5,6,7-tetrahydro-6-aminobenzothiazole 5a or an enantiomer or a salt thereof.

2. A process as claimed in claim 1, wherein the protected cyclohexandione 1p is a cyclic ketal 1r:

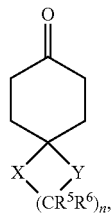

wherein:
X and Y are independently O, S, $NR^7$ or Se;
n is 2 or 3;
$R^5$ and $R^6$ are independently hydrogen or alkyl; and
$R^7$ is hydrogen or alkyl.

3. A process as claimed in claim 1, wherein the protected cyclohexandione 1p is monoethyleneketal 1:

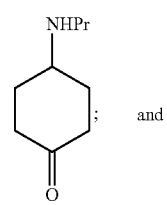

4. A process as claimed in claim 1, wherein $R^3$ is hydrogen.

5. A process as claimed in claim 1, wherein the reductive amination of step (a) is carried out with $NaCNBH_3$.

6. A process as claimed in claim 1, wherein the 2-amino-4,5,6,7-tetrahydro-6-aminobenzothiazole 5a comprises at least 95% of the (R)- or the (S)-enantiomer.

7. A process as claimed in claim 1, for the preparation of a 2-amino-4,5,6,7-tetrahydro-6-aminobenzothiazole di-hydrochloric acid salt:

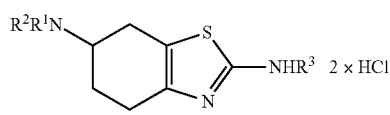

or an enantiomer thereof.

8. A process for the preparation of 2-amino-4,5,6,7-tetrahydro-6-(propylamino)-benzothiazole 5:

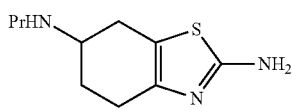

or an enantiomer or a salt thereof, comprising the steps of:

(a) reductively aminating cyclohexandione monoethyleneketal 1 with $PrNH_2$ to yield 4-n-propylamino-cyclohexanone-ethyleneketal 2:

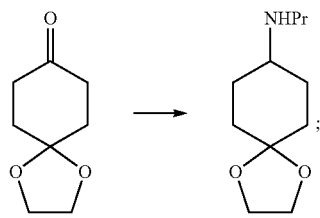

(b) deprotecting 4-n-propylamino-cyclohexanone-ethyleneketal 2 to yield 4-n-propylamino-cyclohexanone 3:

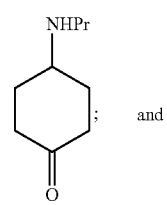

(c) treating 4-n-propylamino-cyclohexanone 3 with iodine and thiourea.

9. A process as claimed in claim 8, for the preparation of (S)-2-amino-4,5,6,7-tetrahydro-6-(propylamino)-benzothiazole I:

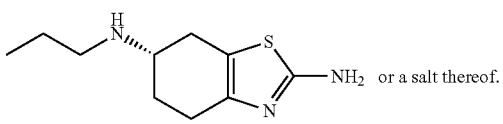

10. A process as claimed in claim 8, for the preparation of (S)-2-amino-4,5,6,7-tetrahydro-6-(propylamino)-benzothiazole di-hydrochloric acid salt:

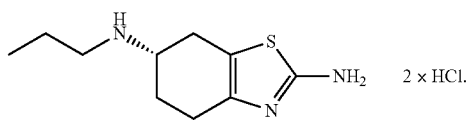

* * * * *

UNITED STATES PATENT AND TRADEMARK OFFICE
CERTIFICATE OF CORRECTION

| | | |
|---|---|---|
| PATENT NO. | : 7,868,029 B2 | |
| APPLICATION NO. | : 10/527844 | |
| DATED | : January 11, 2011 | |
| INVENTOR(S) | : Ashwini Kumar Gupta et al. | |

It is certified that error appears in the above-identified patent and that said Letters Patent is hereby corrected as shown below:

In claim 1 at column 10, line 51, please replace the structure:

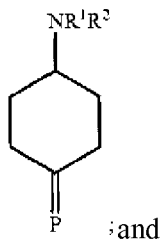 ; and with the structure:

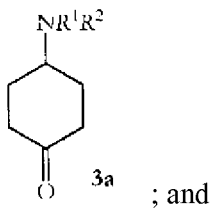 ; and

Signed and Sealed this
Twenty-second Day of March, 2011

David J. Kappos
*Director of the United States Patent and Trademark Office*